United States Patent [19]

Bailey

[11] Patent Number: 4,540,705

[45] Date of Patent: Sep. 10, 1985

[54] ANTIDEPRESSANT IMIDAZOLINES AND RELATED COMPOUNDS

[75] Inventor: Denis M. Bailey, East Greenbush, N.Y.

[73] Assignee: Sterling Drug Inc., New York, N.Y.

[21] Appl. No.: 475,193

[22] Filed: Mar. 14, 1983

[51] Int. Cl.³ .................. A61K 31/415; C07D 233/06; C07D 233/58
[52] U.S. Cl. .................... 514/401; 514/396; 514/400; 544/242; 544/335; 548/335; 548/355
[58] Field of Search .............................. 548/355, 335; 424/273 R

[56] References Cited

U.S. PATENT DOCUMENTS 2,161,938  6/1939  Sonn ..................................... 548/355
2,731,471  1/1956  Synerholm et al. ................. 548/347
3,354,175  11/1967  Fruhstorfer et al. ................ 548/355

FOREIGN PATENT DOCUMENTS 757650  9/1956  United Kingdom ................ 548/347

OTHER PUBLICATIONS

Izquierdo, I., et al., *Revista Farmaceutica* 97, 196–197, (1955).

*Primary Examiner*—Richard A. Schwartz
*Attorney, Agent, or Firm*—Thomas L. Johnson; B. Woodrow Wyatt; Paul E. Dupont

[57] ABSTRACT 2-(2-Naphthalenyl)alkyl-4,5-dihydro-1H-imidazoles and -tetrahydropyrimidines, the corresponding 3,4-dihydronaphthalenyl and 1,2,3,4-tetrahydronaphthalenyl compounds; and the corresponding indene and indane derivatives, useful as antidepressant or diuretic agents, are prepared by reacting the appropriate 2-(cyanoalkyl)naphthalene or -indane derivative (or the corresponding ester or imino-ether) with an alkylenediamine.

21 Claims, No Drawings

ANTIDEPRESSANT IMIDAZOLINES AND RELATED COMPOUNDS

BACKGROUND OF THE INVENTION (1) Field of the Invention

The present invention relates to naphthalene and hydronaphthalene substituted imidazolines and related compounds, useful as antidepressant or diuretic agents, and methods for the preparation thereof.

(2) Information Disclosure Statement

Naphazoline [2-(1-naphthylmethyl)imidazoline], Ciba U.S. Pat. No. 2,161,938 (June 13, 1939); and tetrahydrozoline [2-(1,2,3,4-tetrahydro-1-naphthyl)-2-imidazoline], Sahyun Laboratories U.S. Pat. No. 2,731,471 (Jan. 17, 1956), are well-known sympathomimetic agents used as nasal decongestants. They do not possess $\alpha_2$-adrenergic antagonist activity characteristic of antidepressant agents.

Charles Pfizer & Co. British Pat. No. 757,650, published Sept. 19, 1956, discloses 2-(1-indanyl)imidazoline as having pressor activity. The same compound is also disclosed in Sahyun Laboratories U.S. Pat. No. 2,731,471, loc. cit.

J. A. Izquierdo and M. Giuntti, Revista Farmaceutica 97, 196–197 (1955), describe the preparation of 2-(2-naphthylmethyl)imidazoline:

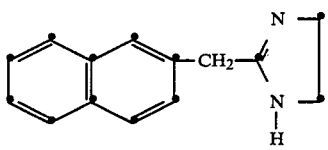

and its effect on blood pressure in dogs and toads.

SUMMARY OF THE INVENTION

In a product aspect, the invention relates to compounds of the formulas:

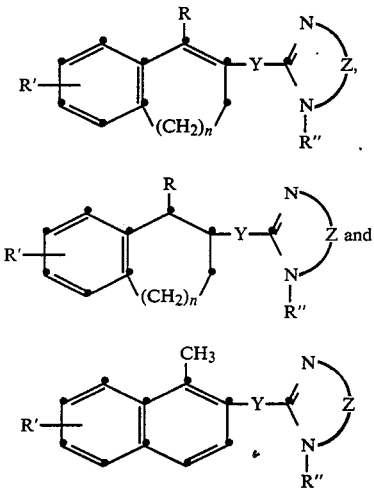

wherein:
R is H or CH$_3$;
R' is hydrogen, lower-alkyl, lower-alkoxy or halo;
R" is hydrogen or lower-alkyl;
n=0 or 1;
Y is an alkylene bridge of 1-2 carbons; and
Z is —C≡C— or an alkylene bridge of 2-3 carbon atoms optionally substituted by one or two alkyl groups of 1-2 carbon atoms;
and pharmaceutically acceptable acid-addition salts thereof.

A preferred class of compounds are those wherein R is CH$_3$, R' and R" are hydrogen, Y and Y' are CH$_2$, and Z is —CH$_2$CH$_2$—.

In a further product aspect, the invention relates to compositions for treating depressed states in warm blooded animals which comprise an antidepressantly effective amount of a compound of Formulas I, II or III together with one or more pharmaceutically acceptable excipients.

In a process aspect, the invention relates to a process for preparing a compound of Formulas I, II or III, wherein Z is a lower-alkylene bridge as defined above, which comprises reacting a compound of one of the formulas

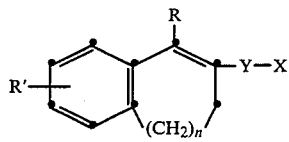

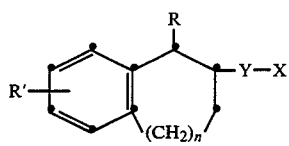

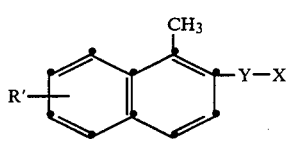

where X is —C≡N, —C(=NH)—O—alkyl or —COO—alkyl, with a compound of the formula H$_2$N—Z—NHR".

In a further process aspect, the invention relates to a method for treating depressed states in warm blooded animals, which comprises administering a composition comprising an antidepressantly effective amount of a compound of Formulas I, II or III.

In a still further process aspect, the invention relates to a method for treating depressed states in warm blooded animals, which comprises administering a composition which comprises an antidepressantly effective amount of 4,5-dihydro-2-(2-naphthalenylmethyl)-1H-imidazole or a pharmaceutically acceptable acid-addition salt thereof together with one or more pharmaceutically acceptable excipients.

DETAILED DESCRIPTION INCLUSIVE OF PREFERRED EMBODIMENTS

In the definition of the variables in Formulas I, II and III above, the term "lower-alkyl" or "lower-alkoxy", used in defining R' or R", stands for alkyl or alkoxy containing one to three carbon atoms, thus including methyl, ethyl, propyl and isopropyl.

In the definition of the variables in Formulas IV, V and VI where X is —C(=NH)—O—alkyl or —COO—alkyl, the alkyl group preferably has from one to five carbon atoms.

The compounds of the invention, where Z is a lower-alkylene bridge as defined above, are prepared by reacting an intermediate of the Formula IV, V or VI with a diamine H₂N—Z—NHR". The reaction takes place at a temperature between about 50° and 150° C. in the presence of a promoter or activating substance. The latter substance is an inorganic or organic acid, including Lewis-type acids, or a compound which generates an acid during the reaction. Examples of such promoters are hydrogen chloride, p-toluenesulfonic acid, carbon disulfide and trimethylaluminum. In the case where the intermediate is an imino ether (X=—C(=NH)—O—alkyl), if the hydrochloride salt of the latter is used, the acid of addition serves as the promoter for the reaction with the diamine.

The compounds of Formula II can alternatively be prepared by catalytic hydrogenation of the compounds of Formula I.

The compounds of the invention where Z is —CH=CH— and R"=H are prepared by heating a compound of Formula IV, V or VI where X is —C≡N with aminoacetaldehyde diethyl acetal [H₂NCH₂CH(OC₂H₅)₂] in acetic acid.

The intermediates of Formula IV where X=—C≡N or —COO—alkyl are prepared by a Wittig-type reaction starting with the appropriate tetralone or indanone derivative:

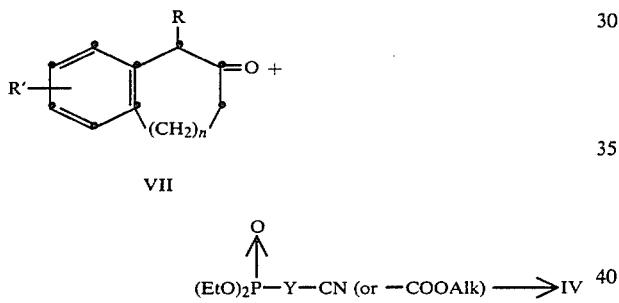

The intermediates of Formula V where X=—C≡N or —COO—alkyl are prepared starting from an unsaturated acid of the formula:

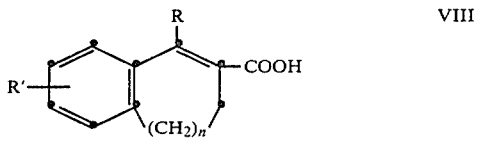

The latter upon reduction with lithium aluminum hydride forms a hydroxymethyl compound of the formula

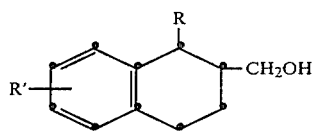

The hydroxymethyl group of IX is then converted by conventional reactions to halomethyl and cyanomethyl (V, X=CN). The latter, if desired, can be converted by acid hydrolysis in the presence of a lower-alkanol to give the corresponding ester (V, X=—COO—alkyl).

The intermediate compounds of Formula VIII above can be prepared by cyclization of the appropriate arylalkyl substituted oxo-esters:

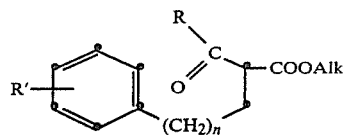

The intermediate of Formula VI where X=—C≡N or —COO—alkyl can be prepared by dehydrogenation of the corresponding compounds of Formula IV, for example, by heating the latter with 2,3-dichloro-5,6-dicyano-1,4-benzoquinone (DDQ).

The compounds of Formula VI where X=—C≡N or —COO—alkyl and Y=CH₂ can alternatively be prepared from acids of the formula:

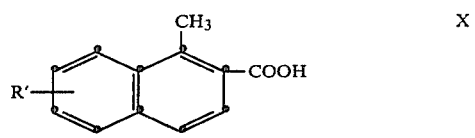

or a lower-alkyl ester thereof. As described above for the acid of Formula VIII, the carboxyl group can be reduced to a hydroxymethyl group and the latter converted to the nitrile (VI; Y=CH₂, X=CN) or ester (VI; Y=CH₂, X=COO—alkyl).

Compounds of Formula IV and VI where Y=CH₂CH₂ can be produced from the homologous acids corresponding to VIII and X where the side chain is —CH₂COOH. The homologous acids can be obtained from VIII or X by the Arndt-Eistert homologation reaction.

The intermediates of Formulas IV, V and VI where X=—C(=NH)—O—alkyl are prepared from the corresponding compounds where X=—C≡N by treating the latter with hydrogen chloride in lower-alkanol solution. The hydrochloride salt of the imino ether is formed.

The invention also contemplates pharmaceutically acceptable acid-addition salts of the compounds of Formulas I, II and III. The nature of the acid-addition salt is immaterial provided it is derived from an acid the anion of which is essentially innocuous to animal organisms. Examples of appropriate acid-addition salts include the hydrochloride, hydrobromide, sulfate, methanesulfonate, maleate, citrate, tartrate, p-toluenesulfonate, cyclohexanesulfamate, and the like salts.

The following examples will further illustrate the invention.

EXAMPLE 1

(a) 3,4-Dihydro-1-methyl-2-naphthaleneacetonitrile [IV; R=CH₃, R'=H, n=1, Y=CH₂, X=CN]

To a stirred suspension of 7.2 g (0.15 mole) of sodium hydride (50% in oil dispersion) in 200 ml of dimethoxyethane was added dropwise 28.1 g (0.15 mole) of diethylcyanomethylphosphonate [(C₂H₅O)₂P(O)CH₂CN]. The addition was complete in ten minutes while the reaction temperature rose to 44° C. The reaction mixture was stirred for 45 minutes and then 25.0 g (0.14 mole) of 1-methyl-2-tetralone was added dropwise over a 30 minute period. The reaction mixture was then warmed at 40° C. for two hours and poured into ice-water. The product was extracted with ether, and the ether extracts were dried over anhydrous magnesium sulfate and concentrated to a yellow oil (31.3 g). The latter was crystallized from ether-hexane to give 3,4-dihydro-1-methyl-2-naphthaleneacetonitrile as a light yellow solid, m.p. 48°–49° C.

(b)
2-[(3,4-Dihydro-1-methyl-2-naphthalenyl)methyl]-4,5-dihydro-1H-imidazole [I; R=CH$_3$, R′ and R″=H, n=1, Y=CH$_2$, Z=CH$_2$CH$_2$]

To a mixture of 60 g (0.33 mole) of 3,4-dihydro-1-methyl-2-naphthaleneacetonitrile and 30 ml of ethylenediamine was added 3 ml of carbon disulfide. The reaction mixture was stirred under nitrogen and heated in an oil bath at 120° C. for 21 hours, and then cooled to room temperature and concentrated in vacuo to remove volatile substances. The solid material was collected, dissolved in 600 ml of chloroform and dried over anhydrous magnesium sulfate. The solvent was removed, and the residue was triturated with ether and dissolved in ethanol. The ethanol solution was acidified with ethanolic hydrogen chloride and ether was added until the solution became cloudy. The solid product which crystallized was collected and dried in vacuo to give 28.7 g of 2-[(3,4-dihydro-1-methyl-2-naphthalenyl)methyl]-4,5-dihydro-1H-imidazole in the form of its monohydrochloride salt, m.p. 223°–224° C. A recrystallization from the same solvent mixture gave a sample with m.p. 226°–229° C.

EXAMPLE 1A (a) Ethyl 3,4-dihydro-1-methyl-2-naphthaleneacetate [IV; R=CH$_3$, R′=H, n=1, Y=CH$_2$, X=COOC$_2$H$_5$]

To a stirred suspension of 24 g (0.5 mole) of sodium hydride (50% in oil dispersion) in 750 ml of dimethoxyethane, cooled to 0° C., was added dropwise over a one hour period a solution of 112.1 g (0.5 mole) of triethyl phosphonoacetate [(C$_2$H$_5$)$_2$OP(O)CH$_2$CO$_2$C$_2$H$_5$] in 140 ml of dimethoxyethane. The reaction mixture was maintained at about 15° C. during the addition and then stirred at room temperature for two hours. It was then cooled to 5° C. and treated dropwise with a solution of 68.7 g (0.386 mole) of 1-methyl-2-tetralone in 70 ml of dimethoxyethane over a period of one hour. The reaction mixture was stirred overnight, then cooled in an ice bath and acidified with 27 ml of glacial acetic acid. The mixture was poured into ice-water and the layers separated. The aqueous layer was extracted with cyclohexane, and the combined organic layers washed with water and saturated sodium chloride solution. The organic solution was dried over anhydrous magnesium sulfate and concentrated to give 95.8 g of ethyl 3,4-dihydro-1-methyl-2-naphthaleneacetate as a yellow liquid.

(b)
2-[(3,4-Dihydro-1-methyl-2-naphthalenyl)methyl]-4,5-dihydro-1H-imidazole [I; R=CH$_3$, R′ and R″=H, n=1, Y=CH$_2$, Z=CH$_2$CH$_2$]

A solution (290 ml) of trimethylaluminum, 2M in toluene (0.58 mole) was added slowly to 500 ml of toluene. The diluted solution was cooled to 0° C. and treated dropwise with 39 ml of ethylenediamine in 40 ml of toluene. The resulting mixture was stirred at room temperature for one hour and then gradually heated. When the temperature of the mixture reached about 70° C., 83.0 g (0.36 mole) of ethyl 3,4-dihydro-1-methyl-2-naphthaleneacetate was added dropwise over a 45 minute period during which time the temperature rose to 100° C. The reaction mixture was heated at reflux (110° C.) for three hours, then cooled to 0° C. and treated dropwise with 150 ml of water. Methanol (500 ml) and 500 ml of methylene dichloride were added, and the mixture was stirred for one hour and filtered through sodium sulfate. The organic layer was separated from the filtrate and concentrated in vacuo. The residue was collected, air dried (60 g) and dissolved in 300 ml of 2-propanol and treated with 108 ml of 2.4M hydrogen chloride in 2-propanol. Upon cooling the solution in an ice-methanol bath, there separated 31.2 g of 2-[(3,4-dihydro-1-methyl-2-naphthalenyl)methyl]-4,5-dihydro-1H-imidazole in the form of its mono-hydrochloride salt. Further recrystallization from 2-propanol gave a sample of the compound with m.p. 230°–232° C.

EXAMPLE 2

(a) 3,4-Dihydro-2-naphthaleneacetonitrile [IV; R and R′=H, n=1, Y=CH$_2$, X=CN] was prepared from 1.45 g of 50% sodium hydride, 67 g of diethyl cyanomethylphosphonate and 4.2 g of 2-tetralone in 40 ml of dimethoxyethane according to the procedure of Example 1(a). The crude product was distilled at 97°–106° C. (0.05 mm) and purified by chromatography using ether-hexane as eluant to give 3.84 g of 3,4-dihydro-2-naphthaleneacetonitrile.

(b) 2-[(3,4-Dihydro-2-naphthalenyl)methyl]-4,5-dihydro-1H-imidazole [I; R, R′ and R″=H, n=1, Y=CH$_2$, Z=CH$_2$CH$_2$] was prepared from 21.5 ml of 2M trimethylaluminum in toluene, 2.9 ml of ethylenediamine, and 3.5 g of 3,4-dihydro-2-naphthaleneacetonitrile according to the procedure of Example 1A, part b. There was obtained 2.4 g of product which when recrystallized first from acetonitrile and then from 2-propanol afforded 1.2 g of 2-[(3,4-dihydro-2-naphthalenyl)methyl]-4,5-dihydro-1H-imidazole in the form of its monohydrochloride salt hydrate (4:1), m.p. 221°–223° C.

EXAMPLE 2A (a) Ethyl 3,4-dihydro-2-naphthaleneacetate [IV; R and R′=H, n=1, Y=CH$_2$, X=COOC$_2$H$_5$] was prepared from 4.2 g of 50% sodium hydride, 20 g of triethyl phosphonoacetate and 10 g of 2-tetralone in dimethoxyethane according to the procedure of Example 1A, part (a). There was obtained 13.2 g of product as a red oil.

(b) 2-[(3,4-Dihydro-2-naphthalenyl)methyl]-4,5-dihydro-1H-imidazole [I; R, R′ and R″=H, n=1, Y=CH$_2$, Z=CH$_2$CH$_2$] was prepared from 280 ml of trimethylaluminum (2M in toluene), 33.8 g of ethylenediamine and 75.6 g of ethyl 3,4-dihydro-2-naphthaleneacetate according to the procedure of Example 1A, part (b). There was obtained 31 g of product of 85% purity which was converted to the mono-hydrochloride salt and recrystallized from ethanol-ether (90:10) to give a sample of the compound, m.p. 235°–237° C., identical to that of Example 2(b) except that no water of crystallization was present.

EXAMPLE 3

2-[(3,4-Dihydro-1-methyl-2-naphthalenyl)methyl]-1,4,5,6-tetrahydropyrimidine [I; R=CH$_3$, R′ and R″=H, n=1, Y=CH$_2$, Z=CH$_2$CH$_2$CH$_2$] was prepared from 1.8 g of 3,4-dihydro-1-methyl-2-naphthaleneacetonitrile, 20 ml of 1,3-propanediamine and 2 drops of carbon disulfide according to the procedure of Example 1, part (b). There was obtained 1.22 g of product in the form of its mono-hydrochloride salt, pale yellow powder, m.p. 201°–203° C.

EXAMPLE 4

(a) Imino-methyl ether derived from 3,4-dihydro-1-methyl-2-naphthaleneacetonitrile [IV; R=$CH_3$, R'=H, n=1, Y=$CH_2$, X=C(O$CH_3$)=NH]

Dry hydrogen chloride was bubbled through a solution of 3.0 g of 3,4-dihydro-1-methyl-2-naphthaleneacetonitrile in 30 ml of methanol and 15 ml of ether for five minutes. The mixture was allowed to stand overnight in a freezer; then 50 ml of ether was added and the mixture cooled in an ice-bath. The resulting solid product comprising the hydrochloride salt of the imino-methyl ether was collected, dried in vacuo and used directly in the next reaction.

(b) 2-[(3,4-Dihydro-1-methyl-2-naphthalenyl)methyl]-4,5-dihydro-1-methyl-1H-imidazole [I; R=$CH_3$, R'=H, R''=$CH_3$, n=1, Y=$CH_2$, Z=$CH_2CH_2$]

A solution of 4.5 g of the imino-ether hydrochloride from part (a) and 1.35 g of N-methylethylenediamine in 30 ml of methanol was heated at reflux for about 20 hours. The reaction mixture was cooled to room temperature and 5 ml of ethanolic hydrogen chloride was added. The solvent was removed in vacuo and the residue triturated with acetone. The acetone soluble material was recovered and recrystallized first from acetonitrile-ether and then from acetone-acetonitrile to give 1.5 g of 2-[(3,4-dihydro-1-methyl-2-naphthalenyl)methyl]-4,5-dihydro-1-methyl-1H-imidazole in the form of its monohydrochloride salt hydrate (3:1), m.p. 162°–164° C.

EXAMPLE 5

2-[(3,4-Dihydro-1-methyl-2-naphthalenyl)methyl]-1-ethyl-4,5-dihydro-1H-imidazole [I; R=$CH_3$, R'=H, R''=$C_2H_5$, n=1, Y=$CH_2$, Z=$CH_2CH_2$] was prepared from 3.8 g of the imino-ether hydrochloride from Example 4, part (a), 1.8 g of N-ethylethylenediamine and 30 ml of methanol according to the procedure of Example 4, part (b). There was obtained 2.05 g of the product in the form of its hydrochloride salt, m.p. 159°–161° C. when recrystallized from acetone.

EXAMPLE 6

2-[(3,4-Dihydro-1-methyl-2-naphthalenyl)methyl]-4,5-dihydro-4-methyl-1H-imidazole [I; R=$CH_3$, R' and R''=H, n=1, Y=$CH_2$, Z=CH($CH_3$)$CH_2$] was prepared from 8 ml of trimethylaluminum (2M in toluene), 1.4 ml of 1,2-diaminopropane and 2.3 g of ethyl 3,4-dihydro-1-methyl-2-naphthaleneacetate (Example 1A, part a) according to the procedure of Example 1A, part (b). The product was obtained in the form of its monohydrochloride salt, m.p. 165°–166° C. when recrystallized from acetone.

EXAMPLE 7

(a) Ethyl 3,4-dihydro-α-methyl-2-naphthaleneacetate [IV; R and R'=H, n=1, Y=CH($CH_3$), X=COO$C_2H_5$] was prepared from 2.0 g of 50% sodium hydride, 8.8 ml of triethyl α-methylphosphonoacetate and 5.8 g of 2-tetralone in dimethoxyethane according to the procedure of Example 1A, part (a). There was obtained 4.8 g of product when chromatographed on silica and eluted with ether-hexane.

(b) 2-[1-(3,4-Dihydro-2-naphthalenyl)ethyl]-4,5-dihydro-1H-imidazole [I; R, R' and R''=H, n=1, Y=CH($CH_3$), Z=$CH_2CH_2$] was prepared from 18 ml of trimethylaluminum (2M in toluene), 2.1 ml of ethylenediamine and 4.0 g of ethyl 3,4-dihydro-α-methyl-2-naphthaleneacetate from part (a) above, according to the procedure of Example 1A, part (b). There was obtained 2.75 g of product in the form of its mono-hydrochloride salt hydrate (4:1), m.p. 182°–185° C. when recrystallized from ethanol-ether.

EXAMPLE 8

(a) 3,4-Dihydro-6-methoxy-1-methyl-2-naphthaleneacetonitrile [IV; R=$CH_3$, R'=6—$CH_3O$, n=1, Y=$CH_2$, X=CN] was prepared from 3.6 g of 50% sodium hydride, 14.2 g of diethyl cyanomethylphosphonate and 14 g of 6-methoxy-1-methyl-2-tetralone (prepared by methylation of 6-methoxy-2-tetralone with methyl iodide) according to the procedure of Example 1(a). There was obtained 9.1 g of product as a yellow oil after chromatography on silica using ether-hexane as eluant.

(b) 2-[(3,4-Dihydro-6-methoxy-1-methyl-2-naphthalenyl)methyl]-4,5-dihydro-1H-imidazole [I; R=$CH_3$, R'=6—$CH_3O$, R''=H, n=1, Y=$CH_2$, Z=$CH_2CH_2$] was prepared from 40 ml of trimethylaluminum (2M in toluene), 4.2 g of ethylenediamine and 8.2 g of 3,4-dihydro-6-methoxy-1-methyl-2-naphthaleneacetonitrile from part (a) above, according to the procedure of Example 1A, part (b). There was obtained 3.5 g of product in the form of its mono-hydrochloride salt, m.p. 205°–207° C. when recrystallized from ethanol-ether.

Similarly, starting from 7-chloro-2-tetralone or 5-methyl-2-tetralone, it is contemplated that there can be prepared 2-[(3,4-dihydro-7-chloro-2-naphthalenyl)methyl]-4,5-dihydro-1H-imidazole [I; R=H, R'=7—Cl, R''=H, n=1, Y=$CH_2$, Z=$CH_2CH_2$] or 2-[(3,4-dihydro-5-methyl-2-naphthalenyl)methyl]-4,5-dihydro-1H-imidazole [I; R=H, R'=5—$CH_3$, R''=H, n=1, Y=$CH_2$, Z=$CH_2CH_2$].

EXAMPLE 9

(a) 3-Methyl-1H-inden-2-ylacetonitrile [IV; R=$CH_3$, R'=H, n=0, Y=$CH_2$, X=CN] was prepared from 3.6 g of 50% sodium hydroxide, 13.3 g of diethyl cyanomethylphosphonate and 9.5 g of 1-methylindan-2-one [Blomquist et al., J. Org. Chem. 26, 3761–9 (1961)] according to the procedure of Example 1(a). There was obtained 4.1 g of product after chromatography on silica using pentane-ether as eluant.

(b) 4,5-Dihydro-2-[(3-methyl-1H-inden-2-yl)methyl]-1H-imidazole [I; R=$CH_3$, R' and R''=H, n=0, Y=$CH_2$, Z=$CH_2CH_2$] was prepared from 25 ml of trimethylaluminum (2M in toluene), 3.2 ml of ethylenediamine and 4.1 g of 3-methyl-1H-inden-2-ylacetonitrile from part (a) above, according to the procedure of Example 1A, part (b). There was obtained 1.5 g of product in the form of its mono-hydrochloride salt, m.p. 255° C. (decompn.) when recrystallized from ethanol.

EXAMPLE 10

(a) Ethyl 1H-inden-2-ylacetate [IV; R and R'=H, n=0, Y=$CH_2$, X=COO$C_2H_5$] was prepared from 3.8 g of 50% sodium hydride, 17.5 g of triethyl phosphonoacetate and 9 g of indan-2-one in dimethoxyethane according to the procedure of Example 1B, part (a). There was obtained 10.6 g of product as a yellow oil.

(b) 4,5-Dihydro-2-[(1H-inden-2-yl)methyl]-1H-imidazole [I; R, R' and R"=H, n=0, Y=CH$_2$, Z=CH$_2$CH$_2$] was prepared from 64 ml of trimethylaluminum (2M in toluene), 8.5 ml of ethylenediamine and 13 g of ethyl 1H-inden-2-ylacetate from part (a) above, according to the procedure of Example 1A, part (b). There was obtained 1.7 g of product in the form of its mono-hydrochloride salt, m.p. 147° C. when recrystallized from ethanol-ether.

EXAMPLE 11

2-[(3,4-Dihydro-1-methyl-2-naphthalenyl)methyl]-1H-imidazole [I; R=CH$_3$, R' and R"=H, n=1, Y=CH$_2$, Z=—CH=CH—]

A mixture of 12.5 g of the imino-methyl ether hydrochloride derived from 3,4-dihydro-1-methyl-2-naphthaleneacetonitrile (Example 4a), 7.2 g of aminoacetaldehyde diethylacetal and 5 ml of acetic acid was heated four hours on a steam bath. Hydrochloric acid (25 ml 6N) was then added, and the mixture was heated for two hours and stirred overnight at room temperature. Volatile materials were removed in vacuo and the residue partitioned between methylene dichloride and hydrochloric acid (2N). The aqueous layer was made basic and extracted with methylene dichloride. The product obtained from the extracts (1.1 g brown solid) was purified by dissolving in methanol and chromatographing on plates using 5% isopropyl alcohol in chloroform, which yielded 500 mg 2-[(3,4-dihydro-1-methyl-2-naphthalenyl)methyl]-1H-imidazole in the free base form, m.p. 209°–211° C.

EXAMPLE 12

2-[(3,4-Dihydro-1-methyl-2-naphthalenyl)methyl]-1,4,5,6-tetrahydro-5,5-dimethylpyrimidine [I; R=CH$_3$, R' and R"=H, n=1, Y=CH$_2$, Z=—CH$_2$C(CH$_3$)$_2$CH$_2$—] was prepared from 1.8 g of 3,4-dihydro-1-methyl-2-naphthaleneacetonitrile and 20 ml of 2,2-dimethyl-1,3-propanediamine and 2 drops of carbon disulfide according to the procedure of Example 1, part (b). There was obtained 0.98 g of product in the form of its monohydrochloride salt, m.p. 180°–182° C.

EXAMPLE 13

2-[(3,4-Dihydro-2-naphthalenyl)methyl]-1,4,5,6-tetrahydro-5,5-dimethylpyrimidine [I; R, R' and R"=H, n=1, Y=CH$_2$, Z=—CH$_2$C(CH$_3$)$_2$CH$_2$—] was prepared from ethyl 3,4-dihydro-2-naphthaleneacetate and 2,2-dimethyl-1,3-propanediamine in the presence of trimethylaluminum according to the procedure of Example 1A, part (b). The product was obtained in the form of its monohydrochloride salt, m.p. 212°–213° C.

EXAMPLE 14

2-[1-(3,4-Dihydro-2-naphthalenyl)ethyl]-1,4,5,6-tetrahydro-5,5-dimethylpyrimidine [I; R, R' and R"=H, n=1, Y=CH(CH$_3$), Z=—CH$_2$C(CH$_3$)$_2$CH$_2$—] was prepared from ethyl 3,4-dihydro-α-methyl-2-naphthaleneacetate (Example 7a) and 2,2-dimethyl-1,3-propanediamine in the presence of trimethylaluminum according to the procedure of Example 1A, part (b). The product was obtained in the free base form, m.p. 152°–153° C.

EXAMPLE 15

(a) 2-Hydroxymethyl-1-methyl-1,2,3,4-tetrahydronaphthalene [IX; R=CH$_3$, R'=H]

To a suspension of 9.5 g of lithium aluminum hydride in tetrahydrofuran was added a solution of 18.75 g of 3,4-dihydro-1-methyl-2-naphthaleneacetic acid (obtained by hydrolysis of the ethyl ester of Example 1A, part a). The reaction mixture was stirred for three hours at room temperature and then treated with 25 ml of saturated sodium potassium tartrate solution. The suspended solids were removed by filtration, washed with ether, and the filtrates concentrated to 17.4 g of an oil. The latter was treated with 20 ml of pentane and chilled in a Dry Ice bath, thereby obtaining 14.5 g 2-hydroxymethyl-1-methyl-1,2,3,4-tetrahydronaphthalene as a colorless solid.

The latter material was converted to its p-toluenesulfonate ester by treating it with 31.3 g p-toluenesulfonyl chloride in 150 ml of pyridine. The ester was obtained in the form of a pale red solid (21.7 g).

(b) 1,2,3,4-Tetrahydro-1-methyl-2-naphthaleneacetonitrile [V; R=CH$_3$, R'=H, n=1, Y=CH$_2$, X=CN]

A mixture of 25.5 g of the p-toluenesulfonate ester of 2-hydroxymethyl-1-methyl-1,2,3,4-tetrahydronaphthalene, 2.25 g of sodium iodide and 7.5 g of sodium cyanide in 150 ml of dimethylformamide was stirred for about 20 hours at room temperature. The reaction mixture was poured into ice and extracted with ether. The extracts were dried over anhydrous magnesium sulfate and concentrated to a brown oil (15.2 g). The latter was treated with pentane to afford 12.5 g of 1,2,3,4-tetrahydro-1-methyl-2-naphthaleneacetonitrile as a colorless solid which melted at room temperature.

(c) trans-4,5-Dihydro-2-[(1,2,3,4-tetrahydro-1-methyl-2-naphthalenyl)methyl]-1H-imidazole [II; R=CH$_3$, R' and R"=H, n=1, Y=CH$_2$, Z=CH$_2$CH$_2$] was prepared from 50 ml of trimethylaluminum (2M in toluene), 6.8 ml of ethylenediamine and 8.9 g of 1,2,3,4-tetrahydro-1-methyl-2-naphthalenylacetonitrile from part (b), according to the procedure of Example 1A, part (b). There was obtained 2.4 g of product in the form of its mono-hydrochloride salt, m.p. 151°–152° C. when recrystallized from acetonitrile-acetone.

EXAMPLE 16 cis-4,5-Dihydro-2-[(1,2,3,4-tetrahydro-1-methyl-2-naphthalenyl)methyl]-1H-imidazole [II; R=CH$_3$, R' and R"=H, n=1, Y=CH$_2$, Z=CH$_2$CH$_2$]

A mixture of 2.0 g of 2-[(3,4-dihydro-1-methyl-2-naphthalenyl)methyl]-4,5-dihydro-1H-imidazole hydrochloride (Example 1b) and 200 mg of palladium-on-carbon catalyst in 100 ml of distilled water was hydrogenated until the mass spectrum showed no evidence of starting material. The product was isolated and recrystallized from ethanol to give 1.7 g of cis-4,5-dihydro-2-[(1,2,3,4-tetrahydro-1-methyl-2-naphthalenyl)methyl]-1H-imidazole in the form of its monohydrochloride salt, m.p. 214.5°–216° C.

By the same hydrogenation procedure it is contemplated that 2-[(3,4-dihydro-2-naphthalenyl)methyl]-4,5-dihydro-1H-imidazole (Example 2b); 2-[(3,4-dihydro-1-methyl-2-naphthalenyl)methyl]-1,4,5,6-tetrahydropyrimidine (Example 3); 2-[(3,4-dihydro-1-methyl-2- naphthalenyl)methyl]-4,5-dihydro-1-methyl-1H-imidazole (Example 4b); 2-[(3,4-dihydro-1-methyl-2-naphthalenyl)methyl]-4,5-dihydro-4-methyl-1H-imidazole (Example 6); 2-[1-(3,4-dihydro-2-naphthalenyl)ethyl]-4,5-dihydro-1H-imidazole (Example 7b); 2-[(3,4-dihydro-6-methoxy-1-methyl-2-naphthalenyl)methyl]-4,5-dihydro-1H-imidazole (Example 8b); 4,5-dihydro-2-[(3-methyl-1H-inden-2-yl)methyl]-1H-imidazole (Example 9b); or 2-[(3,4-dihydro-1-methyl-2-naphthalenyl)methyl]-1H-imidazole can be reduced, respectively, to 2-[(1,2,3,4-tetrahydro-2-naphthalenyl)methyl]-4,5-dihydro-1H-imidazole [II; R, R' and R''=H, n=1, Y=CH$_2$, Z=CH$_2$CH$_2$]; 2-[(1,2,3,4-tetrahydro-1-methyl-2-naphthalenyl)methyl]-1,4,5,6-tetrahydropyrimidine [II; R=CH$_3$, R' and R''=H, n=1, Y=CH$_2$, Z=CH$_2$CH$_2$CH$_2$]; 2-[(1,2,3,4-tetrahydro-1-methyl-2-naphthalenyl)methyl]-4,5-dihydro-1-methyl-1H-imidazole [II; R=CH$_3$, R'=H, R''=CH$_3$, n=1, Y=CH$_2$, Z=CH$_2$CH$_2$]; 2-[(1,2,3,4-tetrahydro-1-methyl-2-naphthalenyl)methyl]-4,5-dihydro-4-methyl-1H-imidazole [II; R=CH$_3$, R' and R''=H, n=1, Y=CH$_2$, Z=CH(CH$_3$)CH$_2$]; 2-[1-(1,2,3,4-tetrahydro-2-naphthalenyl)ethyl]-4,5-dihydro-1H-imidazole [II; R, R' and R''=H, n=1, Y=CH(CH$_3$), Z=CH$_2$CH$_2$]; 2-[(1,2,3,4-tetrahydro-6-methoxy-1-methyl-2-naphthalenyl)methyl]-4,5-dihydro-1H-imidazole [II; R=CH$_3$, R'=6—CH$_3$O, R''=H, n=1, Y=CH$_2$, Z=CH$_2$CH$_2$]; 2-[(3-methyl-1H-indan-2-yl)methyl]-1H-imidazole [II; R=CH$_3$, R' and R''=H, n=0, Y=CH$_2$, Z=CH$_2$CH$_2$]; or 2-[(1,2,3,4-tetrahydro-1-methyl-2-naphthalenyl)methyl]-1H-imidazole [II; R=CH$_3$, R' and R''=H, n=1, Y=CH$_2$, Z=—CH=CH—].

EXAMPLE 17

(a) Methyl 1-methylnaphthalenecarboxylate

A mixture of 24 g of methyl 3,4-dihydro-1-methylnaphthalenecarboxylate, 30 g of 2,3-dichloro-5,6-dicyano-1,4-benzoquinone and 400 ml of toluene was heated at reflux for 18 hours. The reaction mixture was then filtered and concentrated in vacuo. Sodium bisulfite solution (150 ml, 25%) was added to the residue, followed by 150 ml of toluene and 50 ml of ether. The latter mixture was washed twice with each of the following: 25% sodium bisulfite solution, concentrated sodium chloride solution, sodium bicarbonate solution and water. The organic solution was dried over anhydrous sodium sulfate and concentrated in vacuo to give 17.5 g of methyl 1-methylnaphthalenecarboxylate as an oil, which upon further purification gave the product in crystalline form, m.p. 48°–49° C.

(b) 2-Hydroxymethyl-1-methylnaphthalene was prepared from 14 g of methyl 1-methylnaphthalenecarboxylate and 1.7 g of lithium aluminum hydride according to the procedure of Example 15, part (a). There was obtained 11.55 g of product as a colorless solid.

(c) 2-Chloromethyl-1-methylnaphthalene

To a mixture of 10.1 g of 2-hydroxymethyl-1-methylnaphthalene, 14.0 ml of triethylamine and 120 ml of methylene dichloride, cooled in an ice-salt bath was added dropwise 5.5 ml of methanesulfonyl chloride. The reaction mixture was allowed to warm to room temperature, washed with water, dried and concentrated in vacuo to obtain 8.4 g of 2-chloromethyl-1-methylnaphthalene as a waxy solid.

(d) 1-Methylnaphthaleneacetonitrile [VI; R'=H, Y=CH$_2$, X=CN]

A mixture of 6.0 g of 2-chloromethyl-1-methylnaphthalene, 3.0 g of sodium cyanide and 75 ml of dimethylformamide was stirred for two hours at room temperature. Water (150 ml) was then added and stirring continued for one hour longer. The solid which had separated was collected by filtration and dried to give 5.0 g of 1-methylnaphthaleneacetonitrile as a pale tan solid.

(e) 4,5-Dihydro-2-[(1-methyl-2-naphthalenyl)methyl]-1H-imidazole [III; R' and R''=H, Y=CH$_2$, Z=CH$_2$CH$_2$] was prepared from 25 ml of trimethylaluminum (2M in toluene), 3.4 ml of ethylenediamine and 4.3 g of 1-methylnaphthaleneacetonitrile according to the procedure of Example 1A, part (b). There was obtained 2.5 g of product in the form of its hydrochloride salt, m.p. 240°–242° C. when recrystallized from ethanol.

Similarly, it is contemplated that 1-methyl-2-naphthaleneacetic acid or an alkyl ester thereof can be carried through the same reactions described in Example 17 to produce 4,5-dihydro-2-[2-(1-methyl-2-naphthalenyl)ethyl]-1H-imidazole [III; R' and R''=H, Y=CH$_2$CH$_2$, Z=CH$_2$CH$_2$].

EXAMPLE 18

4,5-Dihydro-2-(2-naphthalenylmethyl)-1H-imidazole[2-(2-naphthylmethyl)imidazoline] was prepared from 105 ml of trimethylaluminum (2M in toluene), 13.4 ml of ethylenediamine (2M in toluene), 13.4 ml of ethylenediamine and 16.7 g of 2-naphthaleneacetonitrile according to the procedure of Example 1A, part (b). There was obtained 8.1 g of product in the form of its hydrochloride salt, m.p. 262°–264° C. when recrystallized from ethanol.

It is further contemplated that the compounds of Examples 3, 4(b), 6, 8(b) and 11 can be dehydrogenated (aromatized), as by treatment with 2,3-dichloro-5,6-dicyano-1,4-benzoquinone (see Example 17a) to give, respectively:

2-[(1-methyl-2-naphthalenyl)methyl]-1,4,5,6-tetrahydropyrimidine [III; R' and R''=H, Y=CH$_2$, Z=CH$_2$CH$_2$CH$_2$];

2-[(1-methyl-2-naphthalenyl)methyl]-4,5-dihydro-1-methyl-1H-imidazole [III; R'=H, R''=CH$_3$, Y=CH$_2$, Z=CH$_2$CH$_2$];

2-[(1-methyl-2-naphthalenyl)methyl]-4,5-dihydro-4-methyl-1H-imidazole [III; R' and R''=H, Y=CH$_2$, Z=CH(CH$_3$)CH$_2$];

2-[(6-methoxy-1-methyl-2-naphthalenyl)methyl]-4,5-dihydro-1H-imidazole [III; R'=6—CH$_3$O, R''=H, Y=CH$_2$, Z=CH$_2$CH$_2$]; and 2-[(1-methyl-2-naphthalenyl)methyl]-1H-imidazole [III; R' and R''=H, Y=CH$_2$, Z=—CH=CH—].

Unexpectedly, it has been found that the compounds of the present invention, wherein the heterocyclic side chain is attached to the 2-position of the naphthalene, indane or indene nucleus, possess $\alpha_2$-adrenergic antagonist properties characteristic of antidepressant activity, whereas corresponding compounds wherein the heterocyclic side chain is attached to the 1-position of the naphthalene, indane or indene nucleus, such as naphazoline, tetrahydrozoline and 2-(1-indanyl)imidazoline are essentially devoid of such activity. On the other hand, the sympathomimetic activity characteristic of the latter group of compounds is not present in the compounds of the present invention.

The α₂-adrenergic antagonist activity is measured by three screening methods, described as follows:
(1) Tritiated Clonidine Receptor Binding Assay Affinity is determined by assessing the ability of compounds to displace ³H-clonidine (an α₂-adrenergic agonist) from membranes of rat brain. Homogenates of rat cerebral cortex are incubated with 0.4 nM ³H-clonidine which binds to the α₂-adrenergic binding sites (receptor) present on the membranes of the homogenate. Compounds that bind to the α₂-adrenergic receptor, when added to the incubation mixture, will displace ³H-clonidine from its binding site, thereby diminishing the amount of bound radioactivity. The amount of ³H-clonidine still bound is quantitated by liquid scintillation spectrometry. The results are determined in terms of percent inhibition or as $K_i$ values. $K_i$ is a measure of the apparent affinity of the test substance for the α₂-adrenergic binding site, as determined by the method of Cheng and Prusoff, Biochemical Pharmacology 22, 3099 (1973).

(2) Vas Deferens Assay

Activity is determined by assessing the ability of compounds to antagonize the inhibition of twitch height induced by clonidine in the isolated, electrically stimulated rat vas deferens. Clonidine (10 nM) is added to the tissue bath and percentage inhibition of twitch height is calculated. The tissue is then rinsed to remove clonidine and, when the twitch height has returned to normal, the test compound is added. The ability of clonidine to inhibit twitch height is then again determined, and the clonidine-induced inhibition in the presence of the test compound is used to calculate percent antagonism of clonidine. Results are recorded in terms of percent inhibition at the concentration of antagonist used, or as $pA_2$ values, determined by the Schild method; cf. Tallarida and Murray, Manual of Pharmacologic Calculations, pp. 29–32 (Springer-Verlag, 1981).

(3) In vivo Antagonism of Clonidine-induced Antinociception

The intraperitoneal administration of phenyl-p-quinone (PPQ) to mice elicits a nociceptive response which consists of abdominal writhing and extension of the hind limbs. This writhing response is prevented in mice treated with clonidine. When an α₂-adrenergic antagonist is given prior to clonidine, the mice display the writhing response when PPQ is administered. To groups of thirty male mice for each experiment the test compound dissolved in 0.9% sodium chloride was administered either subcutaneously or orally. Clonidine (0.2 mg/kg) was administered orally when the test compound was given subcutaneously and subcutaneously when the test compound was administered orally. Twenty minutes after the administration of clonidine, PPQ (3 mg/kg) was given intraperitoneally. Beginning five minutes after injection of PPQ, the mice were observed for writhing for a period of five minutes. The number of mice that writhed at least three times during the five minute observation period was counted. The number of mice that writhed was scored for each dose of antagonist, and the percentage reversal of clonidine-induced anti-nociception (analgesia) was calculated by dividing the number of animals writhing by the total number of test animals and multiplying the quotient by 100.

A further measure of potential andidepressant activity was obtained by determining the effectiveness of the compounds of the invention in prevention of tetrabenazine-induced ptosis in mice by the method described by Barnett et al., Int. J. Neuropharmacol. 8, 353–360 (1969). The results were expressed in terms of $ED_{50}$ values (effective dose in 50% of the animals).

The testing results for the compounds of the invention are given in the following Table.

| Compound of Example No. | Clonidine [³H] Binding % I. Conc. (nM) | Rat Vas Deferens % A. Conc. (nM) | Antagonism of Clonidine Analgesia % A. Dose (mg/kg) | ($ED_{50}$-p.o.) | Tetrabenazine Reversal ($ED_{50}$) |
|---|---|---|---|---|---|
| 1(b) | $K_i = 11.9$ | $pA_2 = 7.20$ | 50% at 100 p.o. | 111 | 18 |
| 2(b) | $K_i = 28$ | $pA_2 = 7.76$ | 90% at 100 s.c. | 33 | 284 |
| 3 | $K_i = 334$ | 74%, 15% at 3 | | | |
| 4(b) | 60% at 1000 | 2%, 3% at 500 | 20% at 100 s.c. | | |
| 5 | $K_i = 548$ | 2% at 500 | 20% at 100 s.c. | | |
| 6 | 59% at 1000 | 3% at 1 | 20% at 100 s.c. | | |
| 7(b) | $K_i = 32$ | $pA_2 = 7.43$ | 70% at 30 s.c. | | |
| 8(b) | 53% at 1000 | 1% at 500 | | | |
| 9(b) | $K_i = 7$ | $pA_2 = 7.71$ | 10% at 30 p.o. | | |
| 10(b) | $K_i = 76$ | $pA_2 = 7.19$ | 70% at 10 s.c. | | |
| 11 | $K_i = 88$ | $pA_2 = 6.92$ | 60% at 30 s.c. | | |
| 15(d) | $K_i = 401$ | | 30% at 100 s.c. | | |
| 16 | $K_i = 135$ | $pA_2 = 7.22$ | | | |
| 17(e) | $K_i = 7$ | $pA_2 = 7.35$ | 70% at 100 s.c. | 27 | 3 |
| 18 | $K_i = 48$ | $pA_2 = 7.67$ | 80% at 100 p.o. | 53 | 27 |

The compound of Example 12, 2-[(3,4-dihydro-1-methyl-2-naphthalenyl)methyl]-1,2,5,6-tetrahydro-5,5-dimethylpyrimidine, while apparently devoid of any significant α₂-adrenergic antagonist properties, was found to possess diuretic activity when tested in male rats in comparison with hydrochlorothiazide. At oral dose levels of 30 and 100 mg/kg, the compound of Example 12 was found to be 38 and 94%, respectively, as active as hydrochlorothiazide in increase of sodium excretion.

I claim:
1. A compound of the formula

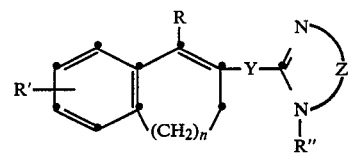

wherein:
R is H or CH₃;
R' is hydrogen, lower-alkyl, lower-alkoxy or halo;
R" is hydrogen or lower-alkyl;
n is 0 or 1;
Y is an alkylene bridge of 1–2 carbons; and Z is —C≡C— or an alkylene bridge of 2 carbon atoms optionally substituted by one or two alkyl groups of 1-2 carbon atoms;

or a pharmaceutically acceptable acid-addition salt thereof.

2. A compound according to claim 1 wherein n is 1, Y is CH₂ and Z is —CH₂CH₂—.

3. 2-[(3,4-Dihydro-1-methyl-2-naphthalenyl)methyl]-4,5-dihydro-1H-imidazole, or an acid-addition salt thereof, according to claim 2.

4. 2-[(3,4-Dihydro-2-naphthalenyl)methyl]-4,5-dihydro-1H-imidazole, or an acid-addition salt thereof, according to claim 2.

5. 2-[(3,4-Dihydro-1-methyl-2-naphthalenyl)methyl]-4,5-dihydro-1-methyl-1H-imidazole, or an acid-addition salt thereof, according to claim 2.

6. 2-[(3,4-Dihydro-1-methyl-2-naphthalenyl)methyl]-1H-imidazole, or an acid-addition salt thereof, according to claim 1.

7. 2-[(3,4-Dihydro-1-methyl-2-naphthalenyl)methyl]-1-ethyl-4,5-dihydro-1H-imidazole, or an acid-addition salt thereof, according to claim 2.

8. 2-[(3,4-Dihydro-1-methyl-2-naphthalenyl)methyl]-4,5-dihydro-4-methyl-1H-imidazole, or an acid-addition salt thereof, according to claim 1.

9. 2-[1-(3,4-Dihydro-2-naphthalenyl)ethyl]-4,5-dihydro-1H-imidazole, or an acid-addition salt thereof, according to claim 1.

10. 2-[(3,4-Dihydro-6-methoxy-1-methyl-2-naphthalenyl)methyl]-4,5-dihydro-1H-imidazole, or an acid-addition salt thereof, according to claim 2.

11. 4,5-Dihydro-2-[(3-methyl-1H-inden-2-yl)methyl]-1H-imidazole, or an acid-addition salt thereof, according to claim 1.

12. 4,5-Dihydro-2-[(1H-inden-2-yl)methyl]-1H-imidazole, or an acid-addition salt thereof, according to claim 1.

13. A composition for treating depressed states in warm blooded animals which comprises an antidepressantly effective amount of a compound according to claim 1 together with one or more pharmaceutically acceptable excipients.

14. A composition according to claim 13 wherein the antidepressantly effective compound is 2-[(3,4-dihydro-1-methyl-2-naphthalenyl)methyl]-4,5-dihydro-1H-imidazole.

15. A method for treating depressed states in warm blooded animals, which comprises administering a composition according to claim 13.

16. A method for treating depressed states in warm blooded animals, which comprises administering a composition according to claim 14.

17. A method for treating depressed states in warm blooded animals, which comprises administering a composition which comprises an antidepressantly effective amount of 4,5-dihydro-2-(2-naphthalenylmethyl)-1H-imidazole or a pharmaceutically acceptable acid-addition salt thereof together with one or more pharmaceutically acceptable excipients.

18. A method for treating depressed states in warm blooded animals, which comprises administering a composition which comprises an antidepressantly effective amount of a compound of the formula

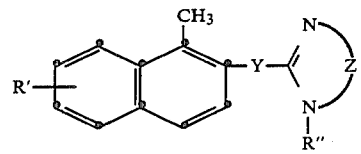

wherein:
R' is hydrogen, lower-alkyl, lower-alkoxy or halo;
R" is hydrogen or lower-alkyl;
Y is an alkylene bridge of 1-2 carbons; and
Z is —C≡C— or an alkylene bridge of 2 carbon atoms optionally substituted by one or two alkyl groups of 1-2 carbon atoms;

or a pharmaceutically acceptable acid-addition salt thereof; together with one or more pharmaceutically acceptable excipients.

19. A method according to claim 18 wherein the antidepressantly effective compound is 4,5-dihydro-2-[(1-methyl-2-naphthalenyl)methyl]-1H-imidazole.

20. A method for treating depressed states in warm blooded animals, which comprises administering a composition which comprises an antidepressantly effective amount of a compound of the formula

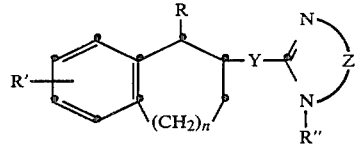

wherein:
R is H or CH₃;
R' is hydrogen, lower-alkyl, lower-alkoxy or halo;
R" is hydrogen or lower-alkyl;
n is 0 or 1;
Y is an alkylene bridge of 1-2 carbons; and
Z is —C≡C— or an alkylene bridge of 2 carbon atoms optionally substituted by one or two alkyl groups of 1-2 carbon atoms;

or a pharmaceutically acceptable acid-addition salt thereof together with one or more pharmaceutically acceptable excipients.

21. A method according to claim 20 wherein the antidepressantly effective compound is 4,5-dihydro-2-[(1,2,3,4-tetrahydro-1-methyl-2-naphthalenyl)methyl]-1H-imidazole, or an acid-addition salt thereof.

* * * * *